United States Patent [19]

Lyons et al.

[11] Patent Number: 5,345,010

[45] Date of Patent: * Sep. 6, 1994

[54] CHROMIA ON METAL OXIDE FOR THE OXIDATION OF ALKANE TO ALCOHOL

[75] Inventors: James E. Lyons, Wallingford; Vincent A. Durante, West Chester, both of Pa.; Darrell W. Walker, Visalia, Calif.

[73] Assignee: Sun Company, Inc. (R&M), Philadelphia, Pa.

[*] Notice: The portion of the term of this patent subsequent to Jun. 15, 2010 has been disclaimed.

[21] Appl. No.: 76,990

[22] Filed: Jun. 15, 1993

Related U.S. Application Data

[63] Continuation-in-part of Ser. No. 905,952, Jun. 29, 1992, Pat. No. 5,220,080.

[51] Int. Cl.$^5$ ............... C07C 29/50; C07C 31/04

[52] U.S. Cl. .................. 568/910; 568/910.5
[58] Field of Search .............. 568/910, 910.5

[56] References Cited

U.S. PATENT DOCUMENTS 2,020,671  11/1935  Dreyfus .................. 568/910
5,220,080   6/1993  Lyons et al. ............. 568/910.5

Primary Examiner—Joseph E. Evans
Attorney, Agent, or Firm—Q. Todd Dickinson; Stephen T. Falk

[57] ABSTRACT

A process for the direct catalytic oxidation of methane to methanol comprises separately contacting chromium chemically bound to the oxygen of a metal oxide support surface with (1) methane and (2) oxidant. The support may comprise silica, alumina, magnesia, titania, or zirconia.

13 Claims, No Drawings

CHROMIA ON METAL OXIDE FOR THE OXIDATION OF ALKANE TO ALCOHOL

This application is a continuation-in-part of the application Ser. No. 07/905,952, filed Jun. 29, 1992, now U.S. Pat. No. 5,220,080.

BACKGROUND OF THE INVENTION

This invention relates to a method for the direct oxidation of light alkanes to form the corresponding alcohols; in particular, the direct catalytic oxidation of methane to methanol. The catalyst found to be useful in the method of this invention comprises chromium oxide chemically bonded to the oxygen atoms attached to a silicon, aluminum, titanium, or magnesium oxide support structure.

BACKGROUND OF THE ART

The ability to directly convert methane to methanol in economically satisfactory yields is an important goal of the oil and gas industry. Methane is an abundant material found world-wide, particularly in the form of natural gas. As a gas, it is difficult and costly to transport. Conversion to the liquid methanol allows for safer, more efficient transportation. In addition, methanol is a valuable commercial feedstock, an important ingredient in the production of reformulated motor fuels, and an environmentally compatible fuel in itself.

The conventional method for the catalytic conversion of methane to methanol involves a first reaction with water to produce synthesis gas, which is a mixture of carbon monoxide and hydrogen, followed by catalytic conversion of the synthesis gas to methanol. A direct, one-step oxidation of methane to methanol would be simpler, and economically and environmentally preferable.

Several catalytic and non-catalytic approaches to directly converting methane to methanol are known in the art. Among these are the following catalytic processes:

United Kingdom Pat. No. 1,244,001 discloses the oxidation of methane to methanol over a catalyst consisting of $(Mo_2O_3) \cdot Fe_2O_3$ on silica/alumina (25% $Al_2O_3$/75% $SiO_2$), sintered to 0.1 g/cm$^2$ at 1000° C., with 65% selectivity (moles Methanol/moles Product $\times$ 100) at 2.1% conversion. The temperature is 439° C. and the pressure 52 atmospheres. Temperatures, pressures and space rates in the process disclosed in this patent are 300°–550° C.; 5–150 atmospheres; and 20,000–50,000 hr$^{-1}$, respectively.

Eusuf, Sci. Res., Dacca (1969) Vol VI, Nos. 1,2, p.16, discloses the oxidation of methane to methanol over $CrO_3$/pumice. The reported results indicated 12% selectivity at 11% $O_2$ conversion. The reported 8.9% methane conversion is noted to most likely be an error as indicated by the reported carbon/oxygen balance. The actual conversion rate may have been far lower.

Further results on the chlorine-promoted oxidation of methane to methanol over $CrO_3$/pumice were reported in Eusuf, Bangl. J. Sci. Ind. Res. (1975) Vol. 10, Nos 1–2, pp. 135–141 ("Eusuf II"). Eusuf II discloses methane conversion as high as 7.3%, with yields of methanol on input methane basis as high as 46.4%. These results were observed at a temperature of 430° C., pressure at 1.5 atmospheres, and a contact time of 1.5 seconds. The reaction was run in the presence of $Cl_2$ at a volumetric ratio of 0.10, $Cl_2:CH_4$, indicating that there was more chlorine gas present than the amount of methane converted in the reaction.

Few, if any, catalysts currently exist, however, which will promote the direct oxidation of methane to methanol in commercially acceptable yield and selectivity. Durante et al, U.S. Pat. No. 4,918,249, assigned to Sun Company, Inc.(R&M), discloses oxidation of methane to methanol in 70% selectivity at 90% oxygen conversion over an iron framework-exchanged sodalite catalyst at temperatures around 415° C.

Most catalysts which contain oxidation-active transition metals do not produce significant amounts of methanol as oxidation product, but rather tend to combust methane to give carbon oxides and water at the elevated temperatures necessary for oxidation to occur. A catalyst which can oxidize methane to methanol at low temperatures could be very important in producing better selectivities by reducing unwanted carbon oxides. The process of the present invention succeeds in achieving higher conversions and methanol selectivities in the direct air oxidation of methane than any other process involving chromium-containing catalysts to date.

The process of the present invention involves direct air or oxygen conversion of methane to methanol. No promoter, such as chlorine gas, need be present, which has the added advantage of avoiding the production of chlorocarbon compounds and the creation of a highly corrosive chlorine-containing reaction system. In an alternative embodiment of the invention, the catalyst serves as regenerable oxidizing reagent which oxidizes alkane and is re-oxidized itself through contact with an oxidizing agent such as air or $O_2$.

SUMMARY OF INVENTION

The present invention comprises a method for the direct conversion of light alkanes to alcohols, aldehydes and other oxidation products comprising contacting said light alkanes with a regenerable oxidizing reagent comprising a surface oxide chromate having the structure:

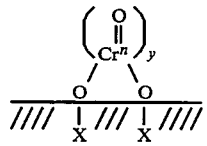

wherein multi-valent chromium moieties are chemically bound to oxygens of a support surface. The support surface is preferably an oxide of X, wherein X comprises an element selected from the group consisting of silicon, aluminum, magnesium, titanium and zirconium. More generally, any suitable solid metal oxide may be used as the support surface. Alternatively, mixed metal oxides, such as silicoaluminates, and zeolites, may also be used. The oxidation state of the chromium, represented by n, is (VI), (IV), or (II) while the number of oxo groups, represented by y, is 2, 1, or 0, respectively.

DETAILED DESCRIPTION OF INVENTION

The direct partial oxidation of methane to methanol has long been problematic. The goal is a desirable one because it holds promise for the utilization of vast methane reserves, principally in the form of natural gas, as methanol for clean-burning fuel and environmentally acceptable fuel additives. Low overall conversion rates and poor selectivity for methanol have previously rendered the process commercially impractical.

The process of the present invention employs a regenerable oxidizing reagent which comprises a chromia moiety chemically bound to a surface support structure. The silica supported compounds of this invention, known as the Phillips Cr/Silica catalyst, have previously been made for use as polymerization catalysts. Their use in the direct conversion of alkanes to alcohols, particularly the oxidation of methane to methanol, is novel.

Regenerable Oxidizing Reagent

The regenerable oxidizing reagents found to be useful in the present invention contain multi-valent chromium bound to oxygen atoms which comprise an integral part of the oxide support structure. The chromium moiety can be present in any of three oxidation states; specifically, chromium(VI)oxo, chromium(IV) oxo, and chromium(II).

According to the present invention, it is believed that in the course of alkane oxidation, the chromium in higher oxidation states is reduced by the alkane. Concurrently with or sequentially to the alkane oxidation, oxidant present in the system re-oxidizes the chromium to the higher oxidation state. Such regeneration of the chromium species can be accomplished apart from the alkane oxidation reaction zone.

The regenerable oxidizing reagents found to be useful in the process of the present invention comprise surface oxide chromates in which chromium is chemically bound to the oxygen of a metal oxide support surface. The preferred surface oxide chromate compounds of use in this invention comprise chromium di-oxo groups chemically bonded to a silicon oxide surface. These silylchromate compounds in their most active state have the general structure:

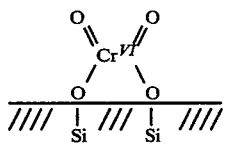

The chromia is believed to be supported on silica in such a way that some or all of the chromia is bonded to surface oxygens. The chromia initially has chromium in oxidation state VI. Chromium(VI) has two oxo oxygens as indicated in the structure above.

One method of making the Phillips Cr/Silica catalysts of this invention is taught in McDaniel and Welch, J. Catal. (1983) 82, 98–118, which is incorporated herein by reference. According to this method, chromia is believed to be deposited on silica such that all or part of the chromia is chromium(VI)di-oxo bound to oxygen atoms of the silica support surface.

Alternative embodiments of the regenerable oxidizing agent useful in the process of this invention comprise chromia chemically bonded to a surface support comprising an oxide of aluminum, magnesium, titanium, zirconium, or other suitable solid metal, or mixtures thereof, such as silicoaluminates. In another embodiment the support surface may comprise zeolite. These compounds can have similar general structures to that depicted above in which the silicon in the oxide surface is replaced by one of the named metals. Similarly to the silica supported compounds described above, these compounds can be prepared in generally the same manner as the silica-supported versions described above, but with a surface support comprising alumina, magnesia, titania, zirconia, other suitable solid metals oxides, or mixed metal oxides.

The concentration of chromia in the silylchromate compound ranges from 0.1 to 1.0 weight percent, preferably 0.5 to 0.6 weight percent, and more preferably 0.6 weight percent. It is believed that approximately 0.6 weight percent chromium provides the most efficient distribution of active chromia moieties on the silica support.

Feedstock

The preferred feedstock for the process of the invention is light alkane, or a mixture of light alkanes, having from 1 to 4 carbon atoms in the molecule. These light alkanes may include methane, ethane, propane, n-butane and isobutane and gaseous mixtures such as natural gas. Among the products of the oxidation are the alcohols corresponding to the particular alkanes which are present in the feedstock.

Reaction Zone

The process of the present invention has been carried out in a glass-lined, tubular reactor. Other conventional reactor configurations can be used as well, which are known to those skilled in the art. The regenerable oxidizing reagent may be maintained within the reaction zone in a variety of reactor bed configurations including fixed beds, fluid beds, ebullating beds and moving beds.

In an alternative embodiment of the invention, the regenerable oxidizing reagent is maintained in a fixed bed and alternately exposed to (1) light alkane and (2) air or $O_2$. In such a system, the oxidizing reagent is reduced during the alkane oxidation step and is then re-oxidized when exposed to the air or $O_2$. A further embodiment employs the regenerable oxidizing reagent in a moving bed whereby the oxidizing reagent can be repetitively transferred from a light alkane zone to an oxidant zone.

Both of these embodiments have the advantage of separately exposing the oxidizing reagent to light alkane and to air or $O_2$. This is advantageous because the light alkane, for example methane, is never directly exposed to the reoxidant, for example $O_2$, thereby avoiding potentially explosive mixtures of methane and $O_2$.

Reaction Conditions

The process of the present invention, particularly the oxidation of methane to methanol, is preferentially carried out in the vapor phase.

In one embodiment, the process is carried out in a fixed bed reaction zone at temperatures between 250° and 550° C., preferably between 350° and 450° C., and more preferably between 400° and 430° C. Pressure in the reaction zone is maintained between 100 and 1500 psig, preferably 700 to 900 psig, and the gas hourly space velocity (GHSV) is in the range of 200 to 25000 $hr^{-1}$, preferably 500 to 12000 $hr^{-1}$. Air or molecular oxygen are the preferred oxidants.

When air is used as the oxidant, light alkane to air mixtures outside the explosive region have been found to be effective. Particularly, oxygen-lean light alkane to air mixtures outside the explosive limit are effective. Mixtures in the neighborhood of 3:1 alkane to air are preferred for laboratory operations. When oxygen is used, an alkane to oxygen ratio of about 14:1 is effective.

demonstrated by the following observations in Examples 2 and 3.

TABLE

OXIDATION OF METHANE OVER CHROMIA ON SILICA[a]

| Catalyst | Temp. (°C.) | Gas Flow (ml/min) | $O_2$ Conv. % | $CH_4$ Conv. % | $CH_3OH$ Produced (mmoles/hr) | $CH_3OH$ Selectivity % |
|---|---|---|---|---|---|---|
| 0.5% $CrO_3/SiO_2$ | 390 | 800 | 15 | 0.6 | 3.9 | 41 |
| " | 400 | 800 | 29 | 1.8 | 10.9 | 38 |
| " | 400 | 200 | 70 | 3.9 | 18.8 | 41 |
| " | 410 | 800 | 38 | 2.0 | 11.8 | 38 |
| " | 420[b] | 800 | 90 | 5.4 | 18.5 | 22 |
| " | 350 | 100 | 15 | 0.4 | 0.3 | 34 |
| " | 300 | 50 | 9 | 0.1–0.2 | <0.1 | 42 |
| 0.6% $CrO_3/SiO_2$ | 390 | 100 | 56 | 3.1 | 2.0 | 32 |
| " | 410 | 95 | 93 | 4.8 | 3.1 | 32 |
| " | 408 | 200 | 99 | 5.0 | 7.3 | 35 |
| " | 418 | 390 | 93 | 5.1 | 15.5 | 37 |
| " | 411 | 800 | 59 | 2.8 | 18.0 | 40 |
| 3% $CrO_3/SiO_2$ | 430 | 800 | 22 | 0.7 | 4.6 | 41 |
| " | 400 | 400 | 18 | 0.7 | 2.5 | 43 |
| " | 400 | 200 | 22 | 0.7 | 0.9 | 33 |
| " | 375 | 200 | 22 | 0.9 | 1.3 | 38 |
| " | 350 | 100 | 22 | 0.9 | 0.3 | 16 |
| " | 300 | 50 | 18 | 0.4 | 0.02 | 4 |

[a]Continuous oxidation of methane (800 psig, 3:1 methane:air raio) over 1.0 cc of catalyst top-loaded into a fully heated 4 cc quartz-lined tubular reactor. Results reported are average of four samples taken at one hour intervals after a two-hour equilibration period.
[b]Exotherm caused internal temperature of 442°C. during reaction.

Without intending to be bound by a particular theory, it is believed that the mechanism of the alkane oxidation reaction involves reduction of the chromium(VI)di-oxo group to chromium(IV) oxo and further to chromium-(II). In the presence of air or oxygen, the oxidizing reagent itself is re-oxidized to its hexavalent state.

According to one embodiment of the present invention, surface silylchromates are used as oxidizing reagents to obtain improved results for the oxidation of alkanes, such as methane, to alcohols. Specifically, the process of this invention achieves greater selectivities and conversions than prior art processes using chromium catalysts for the air-oxidation of methane.

The following examples illustrate the invention:

EXAMPLE 1

The Table shows the results of a series of oxidation reactions comparing the activity of three formulations of the chromia on silica compound as used in the process of the invention. In these oxidation reactions, the ratio of methane to air was 3:1, and the pressure was 800 psig. The vapor phase reaction was conducted continuously over 1.0 cc of catalyst. The results are averages of four samples taken at one hour intervals after a two-hour equilibration period. The reaction runs were performed at various temperatures and flow rates as indicated.

The Table sets forth the percentage of oxygen converted, the percentage of methane converted, the rate of methanol production (in mmoles/hr), and the methanol selectivity of the various reactions. As between the three chromia on silica catalysts, the results indicate that the catalysts containing 0.5 and 0.6 weight percent chromia showed enhanced activity. At 0.6 wt. % chromia, 5.1% methane conversion with 37% methanol selectivity was achieved.

The catalysts employed in the present invention are active at temperatures and pressures below those of previously disclosed processes using chromia catalysts. The regenerable nature of these catalyst compositions is

EXAMPLE 2

Qualitative data regarding alkane oxidation involving the chromia on silica regenerable oxidizing reagent was gathered in a process wherein the chromia reagent was separately exposed to alkane and oxidant. A reactor tube was packed with reagent comprising 0.5–0.6 wt. % chromia. The system was then heated to 250°–350° C. and methane gas was continuously passed over the chromia reagent. In the course of the reaction, the color of the reagent was observed to change from yellow to blue-grey. When oxygen was subsequently passed over the blue-grey chromia reagent at 350°–400° C., the color changed back to yellow. This color change was repeated and observed during successive exposures to methane and oxygen.

EXAMPLE 3

Similarly, isobutane was oxidized over the chromia reagent. At 150° C., isobutane gas was continuously passed over chromia reagent packed in a tubular reactor. The color of the chromia reagent was observed to change from yellow to blue-grey. When the reagent was re-oxidized upon exposure to oxygen at 400° C., the color returned to the initial yellow.

The change in color from yellow to blue-grey is believed to correspond to the reduction of the chromia (VI) moiety as the alkane is oxidized. The change in color is a reliable indicator of the oxidation state of the regenerable oxidizing reagent.

What is claimed is:

1. A method for the direct conversion of light alkane to alcohol comprising separately contacting a regenerable oxidizing reagent with (1) light alkane and (2) oxidant, said reagent comprising a surface oxide chromate in which chromium is chemically bound to oxygen of a metal oxide support surface.

2. The method as claimed in claim 1, wherein said reagent comprises the structure:

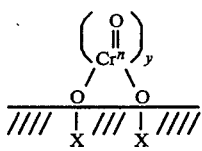

wherein valence n is (VI), (IV), or (II) and y is 2, 1, or 0, respectively; and wherein said chromium is chemically bound to oxygen atoms of said metal oxide support surface comprising oxide of X, wherein X is selected from the group consisting of silicon, aluminum, magnesium, titanium, zirconium and mixtures thereof.

3. The method as claimed in claim 1, wherein said oxidant is selected from the group consisting of oxygen, air, and mixtures thereof.

4. The method as claimed in claim 3, wherein said oxidant is oxygen.

5. The method as claimed in claim 3, wherein said oxidant is air.

6. The method as claimed in claim 1, wherein said reagent is maintained in a reactor bed selected from the group consisting of fixed, fluid, ebullating, and moving beds.

7. The method as claimed in claim 6, wherein said reagent is maintained in a fixed reactor bed.

8. The method as claimed in claim 7, wherein said reagent is alternately exposed to said light alkane and said oxidant.

9. The method as claimed in claim 6, wherein said reagent is maintained in a moving reactor bed.

10. The method as claimed in claim 9, wherein said reagent is moved from a light alkane zone to an oxidant zone.

11. The method as claimed in claim 1, wherein said light alkane comprises compounds selected from the group consisting of methane, ethane, propane, n-butane, isobutane and natural gas or mixtures thereof.

12. The method as claimed in claim 11, wherein said light alkane comprises methane.

13. A method for the direct conversion of light alkane to alcohol comprising separately contacting a regenerable oxidizing reagent comprising a surface oxide chromate in which chromium is chemically bound to a zeolite with (1) light alkane and (2) oxidant, wherein said reagent comprises the structure:

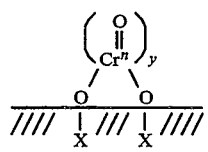

wherein valence n is (VI), (IV), or (II) and y is 2, 1, or 0, respectively; and wherein X is zeolite.

* * * * *